(12) United States Patent
Zhuo et al.

(10) Patent No.: US 9,233,318 B2
(45) Date of Patent: Jan. 12, 2016

(54) PURIFICATION METHOD OF AZACYCLOHEXAPEPTIDE OR ITS SALT

(75) Inventors: Zhonghao Zhuo, Shanghai (CN); Zhijun Tang, Shanghai (CN); Tianhui Xu, Shanghai (CN); Ming Li, Shanghai (CN); Xiaoming Ji, Shanghai (CN); Xiaoliang Gao, Shanghai (CN)

(73) Assignee: SHANGHAI TECHWELL BIOPHARMACEUTICAL CO., LTD., Shanghai (CN)

( * ) Notice: Subject to any disclaimer, the term of this patent is extended or adjusted under 35 U.S.C. 154(b) by 148 days.

(21) Appl. No.: 13/640,836

(22) PCT Filed: Apr. 15, 2011

(86) PCT No.: PCT/CN2011/072833
§ 371 (c)(1),
(2), (4) Date: Oct. 12, 2012

(87) PCT Pub. No.: WO2011/127835
PCT Pub. Date: Oct. 20, 2011

(65) Prior Publication Data
US 2013/0030150 A1 Jan. 31, 2013

(30) Foreign Application Priority Data
Apr. 15, 2010 (CN) .......................... 2010 1 0147002

(51) Int. Cl.
| | | |
|---|---|---|
| *C07K 1/14* | (2006.01) | |
| *C07K 1/16* | (2006.01) | |
| *C07K 1/22* | (2006.01) | |
| *C07K 7/50* | (2006.01) | |
| *B01D 15/26* | (2006.01) | |
| *B01D 15/08* | (2006.01) | |
| *B01D 15/42* | (2006.01) | |
| *C07K 7/54* | (2006.01) | |
| *C07K 1/20* | (2006.01) | |
| *C07K 7/56* | (2006.01) | |

(52) U.S. Cl.
CPC ............ *B01D 15/265* (2013.01); *B01D 15/08* (2013.01); *B01D 15/42* (2013.01); *B01D 15/424* (2013.01); *B01D 15/426* (2013.01); *C07K 1/14* (2013.01); *C07K 1/16* (2013.01); *C07K 1/20* (2013.01); *C07K 1/22* (2013.01); *C07K 7/54* (2013.01); *C07K 7/56* (2013.01)

(58) Field of Classification Search
None
See application file for complete search history.

(56) References Cited

U.S. PATENT DOCUMENTS

| 5,378,804 A | 1/1995 | Balkovec et al. |
| 6,506,726 B1 * | 1/2003 | Dobbins et al. ............... 530/317 |
| 2010/0249371 A1 * | 9/2010 | Gurnani et al. ............... 530/317 |
| 2010/0256074 A1 * | 10/2010 | Eidelman et al. ............ 514/21.1 |

FOREIGN PATENT DOCUMENTS

| CN | 1173875 A | 2/1998 |
| WO | WO 2009/158034 | * 12/2009 |

OTHER PUBLICATIONS

Leonard et al., J. Org. Chem. (2007) 72, 2335-2343.*
International Search Report for PCT/CN2011/072833.
English translation of abstract of CN 1173875 A.

* cited by examiner

*Primary Examiner* — Marcela M Cordero Garcia
*Assistant Examiner* — Catherine Mader
(74) *Attorney, Agent, or Firm* — McClure, Qualey & Rodack, LLP (57) ABSTRACT

A purification method of the compound represented by formula 1 is provided, which includes the following steps: (1) loading crude compound 1 on macroporous adsorbent resin, (2) washing the macroporous adsorbent resin with an aqueous solution, an organic solvent or a mixture solution of organic solvent and water, (3) eluting with an aqueous solution, an organic solvent or a mixture solution of organic solvent and water. The purified compound represented by formula 1 is obtained.

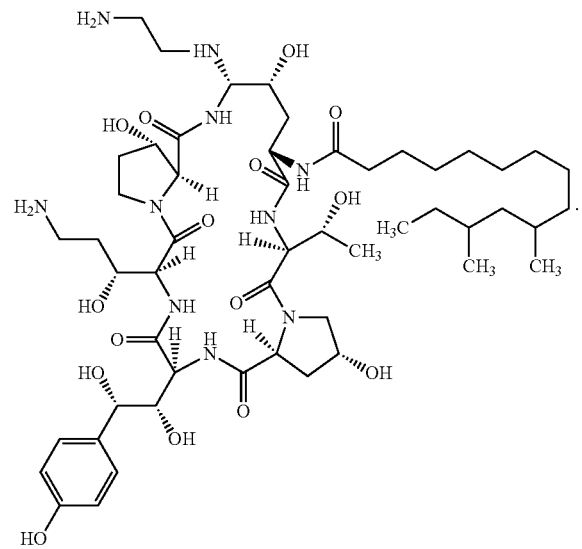

1

11 Claims, 6 Drawing Sheets

PURIFICATION METHOD OF AZACYCLOHEXAPEPTIDE OR ITS SALT

CROSS REFERENCE RELATED APPLICATIONS

This application is a national phase of PCT/CN2011/072833 filed Apr. 15, 2011, which claims priority to China Application Serial No. 201010147002.5, filed Apr. 15, 2010, both of which are entirely incorporated herein by reference.

TECHNICAL FIELD

The invention relates to the field of organic chemistry, particularly to a process for purifying azacyclohexapeptide of Formula 1 or the salts thereof.

BACKGROUND ART

Due to the increasing number of immunodeficiency patients originating from the wide application of invasive therapy and broad-spectrum antibiotics, application of chemotherapy on cancer patients and organ transplant recipients, as well as malignant blood diseases and AIDS, severe and even fatal fungal-infection cases have been significantly increased in recent decades. The use of the antimicrobial drugs has been limited due to the toxicity, drug interaction and resistance.

In 1974, it was discovered that echinocandin compounds possess excellent antibacterial activity. The mechanism for it is that the synthesis of $\beta$-(1,3)-D-glucosan of the pathogenic fungi is blocked, thereby affecting the synthesis of the cellular wall of pathogenic fungi, thus effecting antifungal effect. In 2001, caspofungin was approved by FDA of the United States, which represents the landmark for the research of antifungal medicaments. Caspofungin, the chemical structure of which is shown by Formula 1, was initially developed by Merck Inc. as a broad-spectrum antifungal/antipneumocystosis medicament, and is a low-toxic agent with unique action site and broad spectrum.

In 1994, EP 0620232 disclosed a process for synthesizing and purifying caspofungin from echinocandin $B_0$. Subsequently, U.S. Pat. No. 5,552,521 disclosed a modified process for synthesizing and purifying caspofungin. In both of the two patents, C18 silica gel preparative column chromatography was used for purifying the intermediates and pure products, and freeze drying was used for the collected liquids. However, the use of C18 silica gel column and freeze drying in purifying and drying the intermediates and pure products added operation difficulty for the processes themselves, posed high demand on energy consumption and equipments, and caused serious damage to the equipments, thus making the production on commercial scale impossible.

Therefore, there is still an urgent need in the art to provide a novel process for purifying azacyclohexapeptide of Formula 1 or the salts thereof.

SUMMARY OF THE INVENTION

The subject of the present invention is to provide a novel process for purifying azacyclohexapeptide of Formula 1 or the salts thereof.

In the first aspect of the invention, a process is provided for purifying the compound of Formula 1, said process comprising the following steps:

(1) loading crude compound 1 onto a macroporous adsorption resin;

(2) washing the macroporous adsorption resin with an aqueous solution, an organic solvent or a mixed solution of an organic solvent and water;

(3) eluting with an aqueous solution, an organic solvent or a mixed solution of an organic solvent and water to give a purified compound of Formula 1, The macroporous adsorption resin is selected from a non-polar aromatic adsorption resin polymerized from styrene and divinylbenzene, or a moderately polar methacrylic adsorption resin with methacrylate units in its structure. Preferably, the macroporous adsorption resin is selected from one or more of the following resins: XAD-1, XAD-2, XAD-3, XAD-4, XAD-5, XAD-16, XAD-16HP; or from one or more of the following resins: HP-10, HP-20, HP-20ss, HP-21, HP-30, HP-40, HP-50, SP-825, SP-850, SP-70, SP-700, SP-207; or from one or more of the following resins: XAD-6, XAD-7, XAD-7HP, XAD-8; or HP-2MG.

The organic solvent is selected from $C_1$-$C_4$ alcohol, $C_1$-$C_4$ ketone, acetonitrile or tetrahydrofuran. Preferably, the $C_1$-$C_4$ alcohol is selected from one or more of the followings: methanol, ethanol, propanol, and butanol. The $C_1$-$C_4$ ketone is selected from one or more of the followings: acetone and butanone.

The pH of the aqueous solution, the organic solvent or the mixed solution of an organic solvent and water is ≤7.

Preferably, in step (3), a gradient elution is conducted at an increasing concentration (v/v %) of the organic solvent, when the elution is conducted using the aqueous solution, the organic solvent or the mixed solution.

In another preferred embodiment, step (3) is followed by:

(4) crystallizing the purified compound of Formula 1 to give a compound of Formula 1 having a purity of greater than 99%.

In the second aspect of the invention, a compound of Formula 1 having a purity of greater than 99% is provided, wherein said compound is obtained by the purification process according to the invention as described above.

In the third aspect of the invention, a crystal of the compound of Formula 1 having a purity of greater than 99% as described above is provided. The X-ray powder diffraction (XRPD) pattern of the crystal shows characteristic peaks at the following 2θ diffraction angles: 2.940±0.2°, 5.061±0.2°, 5.880±0.2° and 8.960±0.2°. Preferably, the X-ray powder diffraction (XRPD) pattern of the crystal further shows characteristic peaks at the following 2θ diffraction angles: 6.661±0.2°, 10.299±0.2° and 17.900±0.2°.

Figure 5:
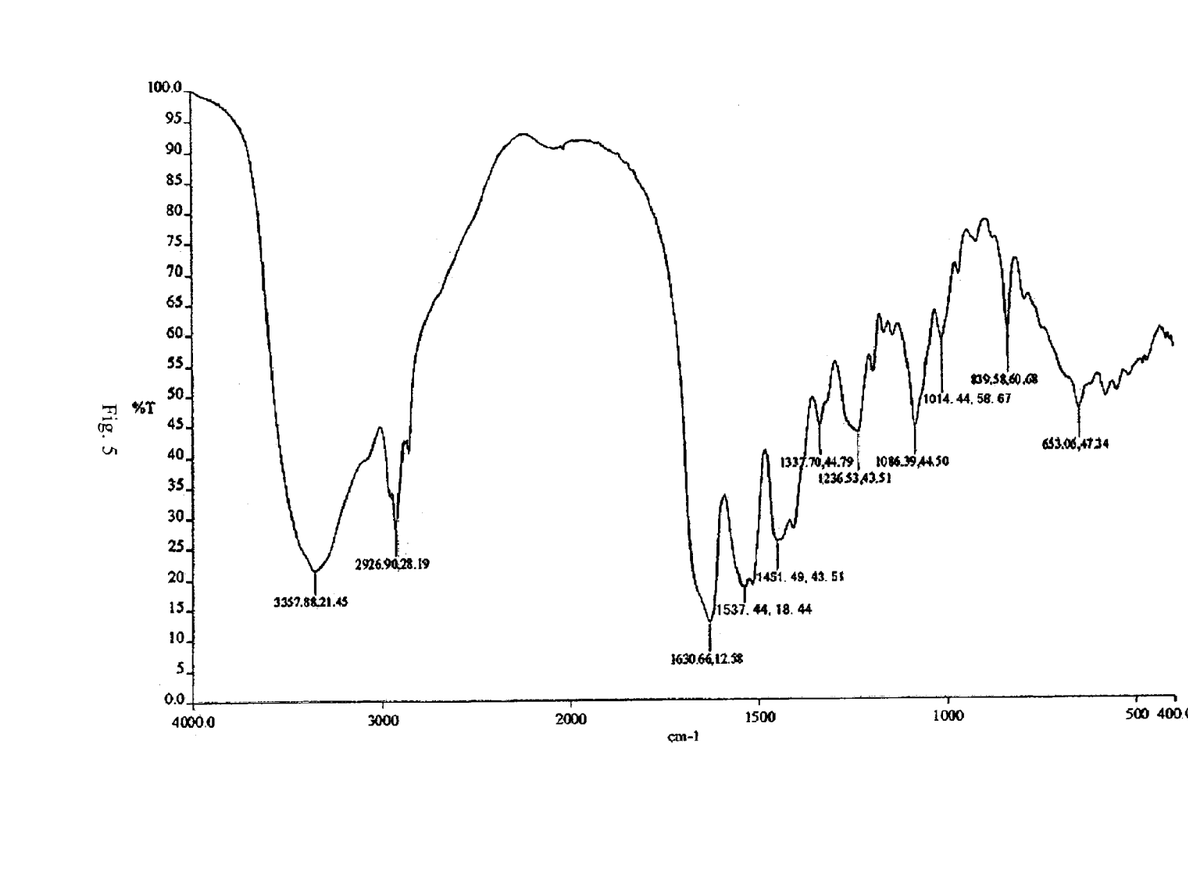
FIG. 5 shows the IR spectrum of caspofungin acetate obtained according to Example 3 of the invention.

The crystal has an IR spectrogram shown in FIG. 5. There is a maximum endothermic peak between 140-146° C. in the differential scanning calorimetry (DSC) graph for the crystal.

Accordingly, a novel process for purifying azacyclohexapeptide of Formula 1 or the salts thereof is provided in the invention.

BRIEF DESCRIPTION OF THE DRAWINGS

In the above HPLC chromatograms, "RT" represents retention time, "Area" represents peak area, "% Area" represents the percentage of a peak area over the total peak area, and "Height" represents peak height.

DETAILED DESCRIPTION OF THE INVENTION

The inventors have discovered that compound 1 can be isolated and purified well using a macroporous adsorption resin under certain conditions.

As used herein, "compound of Formula 1" and "compound 1" can be used interchangeably, both referring to a compound having the following structure or the pharmaceutically acceptable salts thereof:

As used herein, "pharmaceutically acceptable salt" means a salt formed from an acid selected from hydrochloric acid, hydrobromic acid, phosphoric acid, sulfuric acid, maleic acid, citric acid, acetic acid, tartaric acid, succinic acid, oxalic acid, malic acid, glutamic acid, or other acids corresponding to any pharmaceutically acceptable salts listed in Journal of Pharmaceutical Science, 66:2 (1977).

As used herein, "purity of the compound of Formula 1", "purity of compound 1" and "HPLC purity of compound 1" can be used interchangeably, all referring to the percentage of the peak area of compound 1 over the sum of all peak areas as measured under the detecting conditions of high performance liquid chromatography (HPLC) according to the invention.

As used herein, "crude compound of Formula 1" and "crude compound 1" can be used interchangeably, both referring to a mixture containing <90% of compound 1 as measured under the detecting conditions of high performance liquid chromatography (HPLC) according to the invention. Crude compound 1 can be obtained using any suitable process known in the art, including for example but not limited to the processes described in Example 1 of U.S. Pat. No. 5,552,521A and Examples 1-7 of CN101648994A, wherein crude compound 1 was obtained via multi-step chemical reactions using the microbial fermentation product, pneumocandin B0, as the starting material.

As used herein, "solution containing crude compound of Formula 1" and "solution containing crude compound 1" can be used interchangeably, both referring to a solution which contains the target compound 1 and one or more non-target compounds, and may be obtained by dissolving the crude compound 1 in water or a buffer solution of pH ≤ 7, or by mixing a reaction solution containing compound 1 from any process with water or a buffer solution of pH≤7 to give an organic solvent-containing mixed solution. A reaction solution containing compound 1 from any process known in the art for preparing compound 1 can be used, including for example but not limited to a reaction solution obtained via multi-step chemical reactions using the microbial fermentation product, pneumocandin B0, as the starting material. For example, according to the synthesis process reported in U.S. Pat. No. 5,552,521A, the active amide group on pneumocandin $B_0$ was reduced with borane to give an amine, and then the active hydroxyl group on the amine reacted with a compound having a good leaving group such as thiophenol to give a phenyl sulfide. The phenyl sulfide was then ammonolyzed with ethylene diamine in methanol to give a reaction solution of compound 1 in methanol (see the scheme below)

-continued

4

1

The process described in Chinese Patent Application CN101648994A may also be used, wherein the active hydroxyl group on pneumocandin $B_0$, which was a microbial fermentation product and used as the starting material, reacted with a compound having a good leaving group such as thiophenol to give a phenyl sulfide, and the phenyl sulfide was ammonolyzed with ethylene diamine in methanol to give an amine. The amine was then reduced with borane in tetrahydrofuran to give a reaction solution of compound 1 in tetrahydrofuran (see the scheme below):

-continued

The reaction solutions of compound 1 mentioned above are merely some examples, and the reaction solutions of compound 1 according to the invention should not be limited to these examples.

As used herein, "macroporous adsorption resin" mainly includes: (a) a non-polar aromatic adsorption resin polymerized from styrene and divinylbenzene, for example, XAD series adsorption resins (Rohm & Haas Inc., USA), such as XAD-1, XAD-2, XAD-3, XAD-4, XAD-5, XAD-16, XAD-16HP or mixtures thereof, and Diaion HP series adsorption resins (Mitsubishi Inc., Japan), such as HP-10, HP-20, HP-20ss, HP-21, HP-30, HP-40, HP-50, SP-825, SP-850, SP-70, SP-700, SP-207 or mixtures thereof; and (b) a moderately polar methacrylic adsorption resin with methacrylate units in its structure, for example, XAD series adsorption resins (Rohm & Haas Inc., USA), such as XAD-6, XAD-7, XAD-7HP, XAD-8 or mixtures thereof, or Diaion HP series adsorption resins (Mitsubishi Inc., Japan), such as HP-2MG.

As used herein, "loading" refers to the process of bringing a solution containing crude compound 1 into contact with macroporous adsorption resin so that the crude compound 1 is adsorbed onto the macroporous adsorption resin. "Contacting" includes placing macroporous adsorption resin into the solution directly and then agitating to allow the adsorption to occur, or disposing macroporous adsorption resin in a chromatographic device and making the solution flow through the chromatographic column.

"Washing" the macroporous adsorption resin means that a suitable buffer solution is allowed to flow through or over the macroporous adsorption resin.

As used herein, a "washing buffer solution" refers to a buffer solution used to wash the macroporous adsorption resin (mainly for removing organic phase) before the target compound 1 is eluted. Conveniently, the washing buffer solution and the sample-loading buffer solution may, but not necessarily, have the same pH.

"Eluting" molecules from the macroporous adsorption resin means that the molecules are removed from the macroporous adsorption resin by changing the polarity of the buffer solution around the macroporous adsorption resin. Due to the polarity, the buffer solution can compete with the molecules for the adsorption sites on the macroporous adsorption resin.

As used herein, an "elution buffer solution" is used to elute the target compound 1 from a stationary phase. The target compound 1 can be eluted from macroporous adsorption resin by means of the pH of the elution buffer solution.

"Purifying" the compound 1 from a composition comprising the target compound 1 and one or more non-target compounds means that the purity of compound 1 in the composition is increased by removing (totally or partially) at least one non-target compound from the composition.

A process for purifying a compound of Formula 1 according to the invention comprises the following steps:

(1) loading the crude compound 1 onto the macroporous adsorption resin;

(2) washing the macroporous adsorption resin with an aqueous solution, an organic solvent or a mixed solution of an organic solvent and water;

(3) eluting with an aqueous solution, an organic solvent or a mixed solution of an organic solvent and water to give a purified compound 1 (purity ≥90%).

The above step (3) of the purification process can be followed by a crystallization step to obtain compound 1 with high purity (purity ≥99%).

In one embodiment of the invention, the purification process comprises the following steps:

firstly, loading a crude compound 1 onto a macroporous adsorption resin;

secondly, washing the macroporous adsorption resin with great amount of aqueous solution to remove the organic phase; and thirdly, eluting with a mixed solution of an organic solvent and water in gradient mode wherein the organic solvent is used in two or more concentrations from low to high between 5%-95% (v/v %), and then collecting and combining the qualified effluents (with compound 1 having a purity of ≥90%) to give a purified compound 1 (purity ≥90%).

The third step of the purification process described above can be followed by the fourth step, wherein the purified compound 1 (purity ≥90%) is mixed with a dissolving solution (ethanol/water/acetic acid), then ethyl acetate is added dropwise to induce crystallization, and high-purity compound 1 (purity ≥99%) is obtained after filtration.

In the first step, "loading" means bringing a solution containing crude compound 1 into contact with a macroporous adsorption resin, wherein pH value of the solution containing crude compound 1 is ≤7, preferably in the range of 4.5-6.0, and more preferably in the range of 5.0-5.5. The solution containing crude compound 1 may be formed by diluting the reaction solution containing compound 1 with water directly to give a solution containing less than 10% of organic solvent, and then adjusting the pH value to ≤7 with a routine acid, such as acetic acid, hydrochloric acid and the like.

In another embodiment of the invention, the purification process comprises the following steps:

A. bringing a solution containing crude compound 1 into contact with a macroporous adsorption resin;

B. separating the solution containing crude compound 1 from the resin;

C. washing the macroporous adsorption resin from Step B with a washing solution selected from an aqueous solution, an organic solvent or a mixed solution thereof;

D. bringing the washed macroporous adsorption resin obtained from Step C into contact with an elution solution selected from an aqueous solution, an organic solvent or a mixed solution thereof, and then collecting the effluent containing compound 1; and E. concentrating the collected effluent under reduced pressure to dry, and then crystallizing to obtain high-purity compound 1 (purity ≥99%).

Said separation in Step B includes filtration.

The requirements on the purification process for compound 1 are very strict, since compound 1 is not stable. Compound 1 is clinically used in the form of acetate, therefore, the purification process of the invention is illustrated using the acetate thereof, wherein:

firstly, the reaction solution containing compound 1 is diluted with water directly to form a solution containing less than 10% of organic solvent. The pH value of the solution is regulated with acetic acid to ≤7, and then adsorption is conducted using pretreated macroporous adsorption resin. The macroporous adsorption resin is washed with great amount of aqueous solution of acetic acid with pH≤7 to remove the organic phase. Then, the macroporous adsorption resin is eluted in gradient mode with a aqueous solution of acetic acid, wherein the pH of the solution is ≤7 and the concentration of the organic solvent is in the range of 5%-95%. Qualified effluents are collected and pooled. After concentration and crystallization, acetate of compound 1 with high purity (purity ≥99%) is obtained as white crystalline powder.

The X-ray powder diffraction (XRPD) pattern of the acetate crystal for caspofungin shows characteristic peaks at the following 2θ diffraction angles: 2.940±0.2°, 5.061±0.2°, 5.880±0.2° and 8.960±0.2°. Preferably, the X-ray powder diffraction (XRPD) pattern further shows characteristic peaks at the following 2θ diffraction angles: 6.661±0.2°, 10.299±0.2° and 17.900±0.2°.

In all purification processes of the invention, pH of the aqueous solution is ≤7, preferably in the range of 4.5-6.0, and more preferably in the range of 5.0-5.5. The aqueous solution includes acetic acid solution, hydrochloric acid solution and the like.

In all purification processes of the invention, the mixed solution of an organic solvent and water comprises 5%-95%, preferably 10%-60% (v/v) of the organic solvent by the total volume of the mixed solution.

In all purification processes of the invention, the organic solvent is selected from $C_1$-$C_4$ alcohol, $C_1$-$C_4$ ketone, acetonitrile or tetrahydrofuran. The $C_1$-$C_4$ alcohol is selected from one or more of the followings: methanol, ethanol, propanol, and butanol. The $C_1$-$C_4$ ketone is selected from one or more of the followings: acetone and butanone.

All the features mentioned above or in the examples below of the invention can be optionally combined. All features disclosed in this specification may be used in any combination. Any alternative feature serving the same, equivalent, or similar purpose may replace each feature disclosed in this specification. Therefore, unless otherwise specified, the features as disclosed are only general examples of equivalent or similar features.

The advantages of the invention mainly include:

1. A novel low-cost process for purifying azacyclohexapeptide, particularly echinocandin compounds is provided;

2. The advantages of purifying steps in the process according to the invention, such as, simple route, mild conditions, high yields, simple treatments and the like, to a great extent, reduce the requirements on process manipulation and equipments as well as the cost;

3. Stable target compounds can be obtained through the process of the invention, thereby facilitating the quality control on final products and industrial production.

The invention will be further illustrated with reference to the following specific examples. It is to be understood that these examples are only intended to illustrate the invention, but not to limit the scope of the invention. For the experimental methods in the following examples without particular conditions, they are performed under routine conditions or as instructed by the manufacturer. Unless otherwise specified, all percentages, ratios, proportions or parts are by weight.

The unit of the weight/volume percentages in the invention is well known to the skilled in the art, for example, the weight of a solute in a 100 mL solution.

Unless otherwise defined, all scientific and technical terms used herein have the same meaning as commonly understood by the skilled in the art. Furthermore, any process or material similar or equivalent to those described herein can be used in the process of the present invention. The preferred embodiments and materials described herein are merely provided for illustration.

Conditions for detecting the samples of the invention (compound 1) by high performance liquid chromatography:

Chromatograph: Waters High Performance Liquid Chromatography System

Chromatographic column: Kromasil ODS 250*4.6 mm, 5 μm

Mobile phase A: 0.1% (V/V) aqueous perchloric acid solution

Mobile phase B: acetonitrile

Procedure:

| Time (min) | Mobile phase A (%) | Mobile phase B (%) |
|---|---|---|
| 0 | 65.5 | 34.5 |
| 6 | 65.5 | 34.5 |
| 26 | 50 | 50 |
| 28 | 100 | 0 |
| 29 | 65.5 | 34.5 |

Injection volume: 10 μL

Column temperature: 35° C.

Detection wavelength: 220 nm

Flow rate: 1.0 ml/min

Example 1

Figure 1:
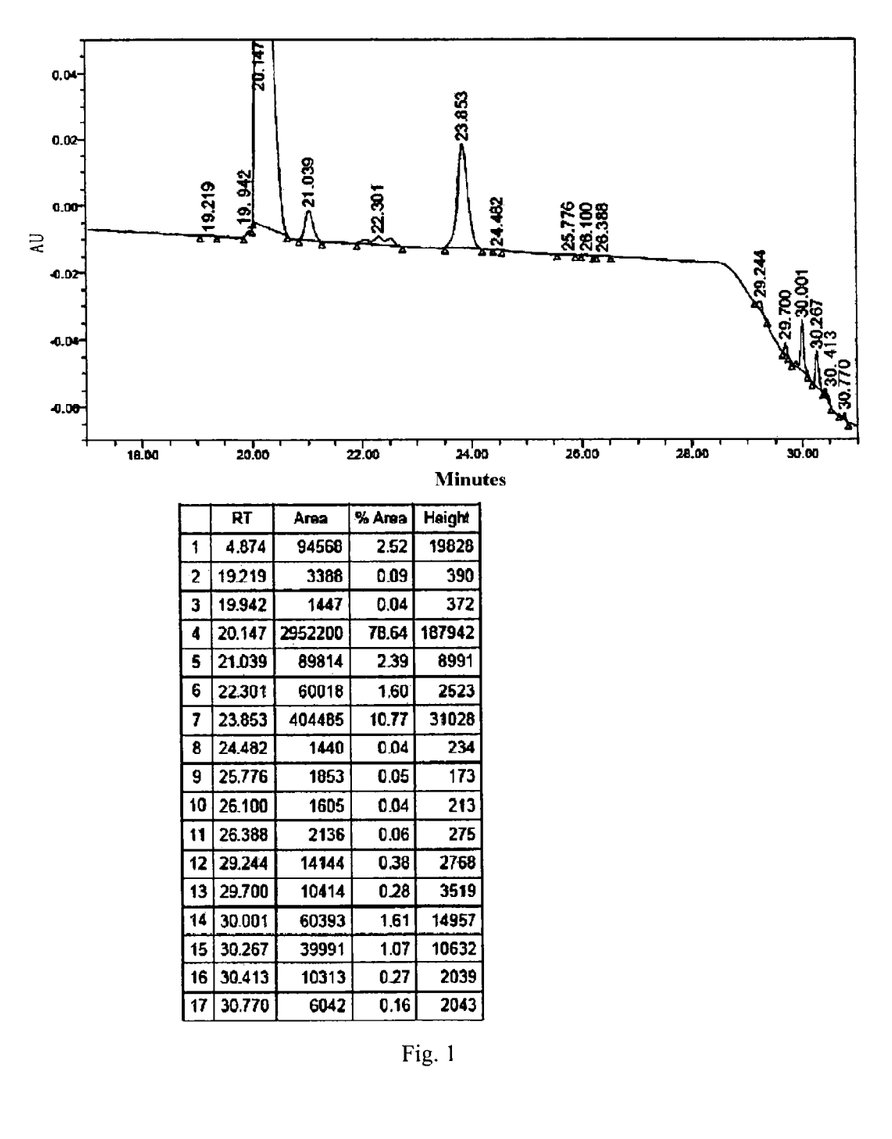
FIG. 1 shows the HPLC chromatogram of a crude compound 1 synthesized via the synthesis route according to U.S. Pat. No. 5,552,521A.

Synthesis of Compound 1 According to U.S. Pat. No. 5,552,521A 500 mL reaction solution containing compound 1 was obtained according to the synthetic route disclosed in U.S. Pat. No. 5,552,521A from $B_0$ (45.0 g, 42.24 mmol). The purity of the product to be purified was 78.64% as measured by HPLC (FIG. 1).

Example 2

Figure 2:
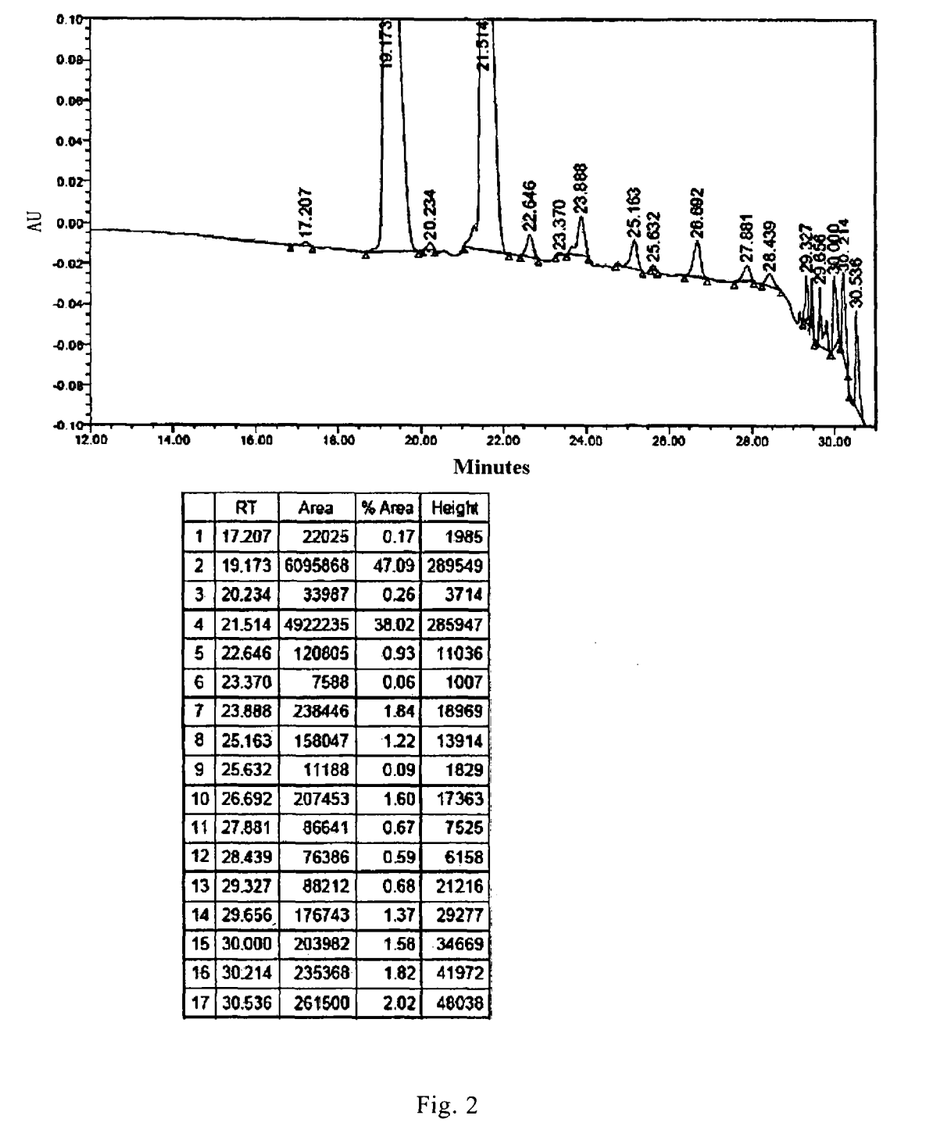
FIG. 2 shows the HPLC chromatogram of a crude compound 1 synthesized via the synthesis route according to CN101648994A.

Synthesis of Compound 1 According to CN101648994A 1.6 L reaction solution containing compound 1 was obtained according to the synthetic route disclosed in CN101648994A from $B_0$ (50.0 g, 47 mmol). The purity of the product to be purified was 47.09% as measured by HPLC (FIG. 2).

Example 3

Purification of Compound 1

At a temperature below 20□, 30 mL reaction solution containing compound 1 (obtained in Example 1) was diluted into 250 mL purified water. The pH was regulated to 5.0-5.5 with acetic acid. Adsorption was conducted using 100 mL pre-treated HP20ss resin at a flow rate of 1 L/h. The resin was washed with 300 mL 0.016% (V/V) acetic acid solution of pH 5-5.5 to remove organic phase. Then, the resin was eluted sequentially in three gradients with 0.016% (V/V) aqueous acetic acid solutions, wherein the pH of the solution was 5-5.5 and the solution contained 10%, 20% and 25% of acetone. Qualified effluents (purity ≥90%) were collected and pooled. About four column volumes of the effluent were collected, and then concentrated to dry.

Figure 3:
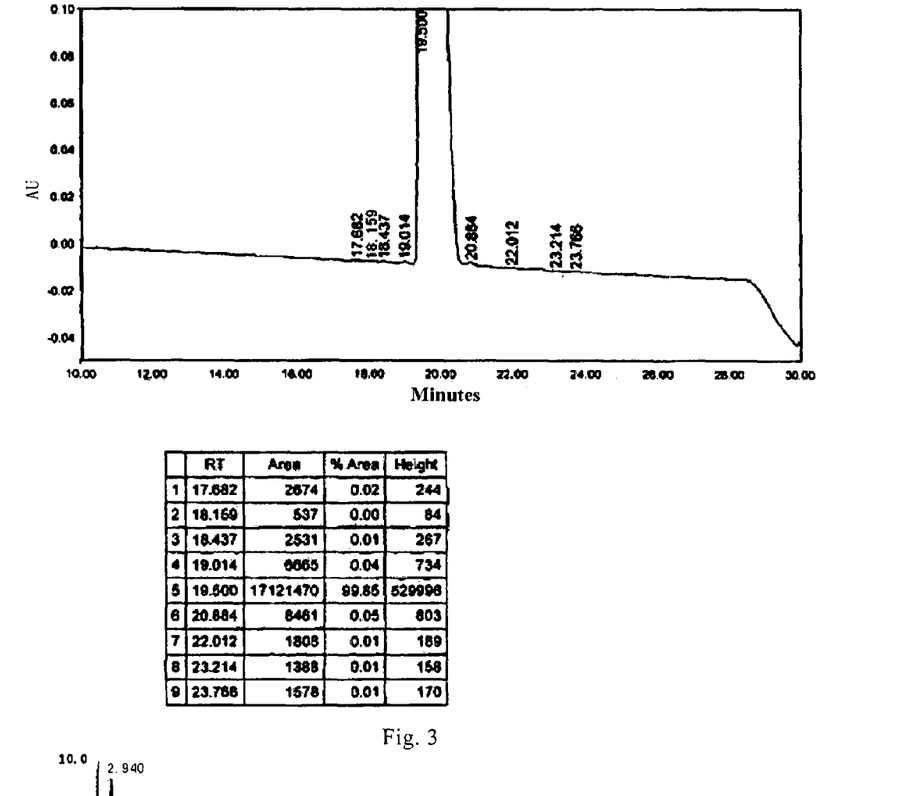
FIG. 3 shows the HPLC chromatogram of caspofungin acetate obtained according to Example 3 of the invention.

The resulted compound 1 with purity ≥90% was dissolved in 7.3 mL dissolving solution of ethanol/water/acetic acid=207.8/19.4/1 (v/v/v), and then induced to crystallize at room temperature by adding ethyl acetate dropwise. After addition, the solution was agitated for 1 hour while the temperature was held constant. After filtration, the filter cake was washed with a solution of water:ethanol:ethyl acetate=1.0:10.7:17.1 to give a white crystalline solid, i.e. caspafungin acetate (0.73 g, purity=99.85%) (FIG. 3).

Figure 4:
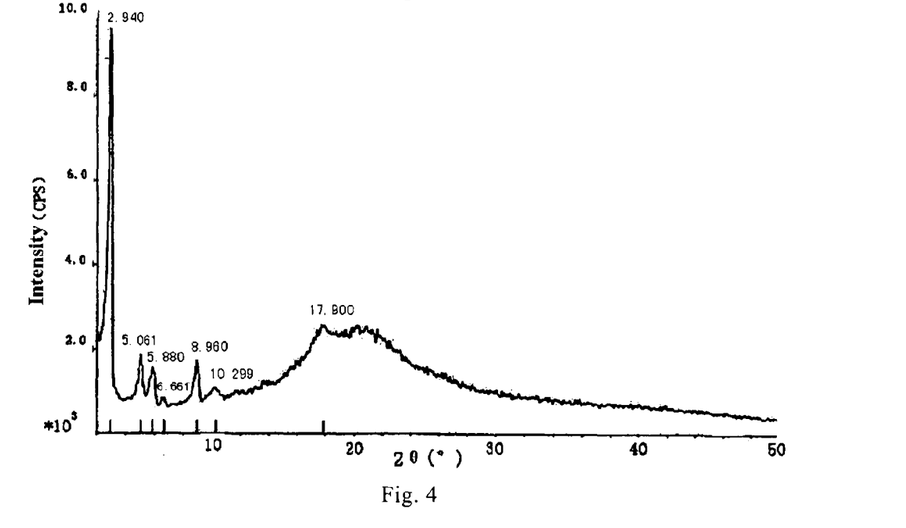
FIG. 4 shows the XRPD pattern of caspofungin acetate obtained according to Example 3 of the invention.

The white powder of caspofungin acetate was detected using RIGAKU D/max 2550VB/PC X-ray Diffractometer at a scanning speed of 2°/min. And the copper radiation target was used. The resulted X-ray powder diffraction pattern was shown in FIG. 4.

The white powder of caspofungin acetate was detected using PE SPEGRUM 1B IR Spectrometer. The resulted IR spectrum was shown in FIG. 5.

Figure 6:
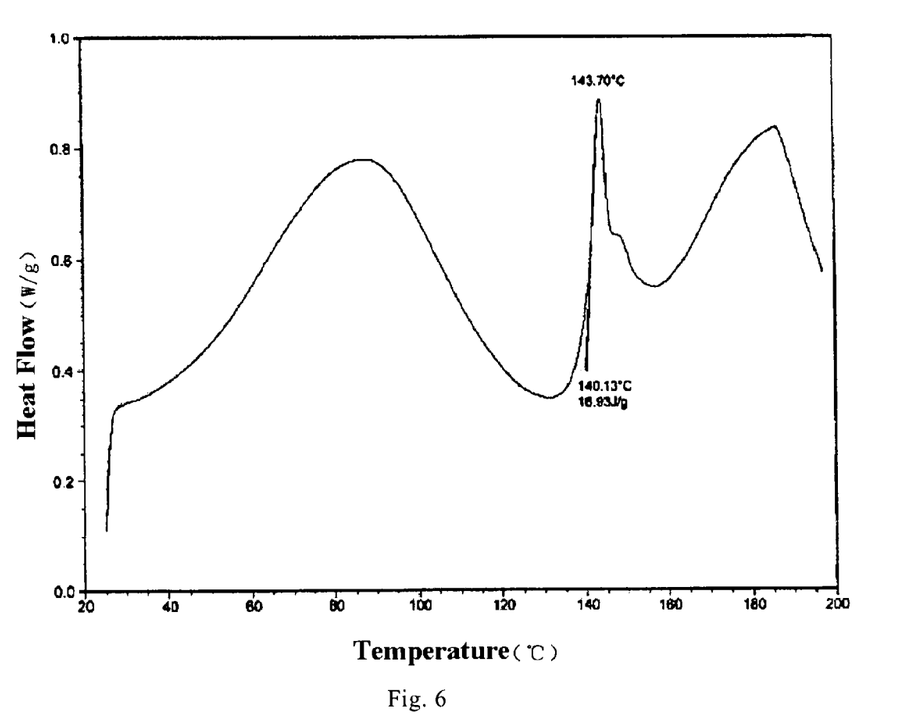
FIG. 6 shows the DSC graph of caspofungin acetate obtained according to Example 3 of the invention.

The white powder of caspofungin acetate was detected using WATERS Q20 Differential Scanning calorimeter. The resulted DSC graph was shown in FIG. 6.

Example 4

Purification of Compound 1

At a temperature below 20□, 30 mL reaction solution of compound 1 (obtained in Example 1) was diluted into 250 mL purified water. The pH was regulated to 5.0-5.5 with acetic acid. Adsorption was conducted using 100 mL pre-treated HP20ss resin at a flow rate of 1 L/h. The resin was washed with 300 mL 0.016% (V/V) acetic acid solution of pH 5-5.5 to remove organic phase. Then, the resin was eluted sequentially in three gradients with 0.016% (V/V) aqueous acetic acid solutions, wherein the pH of the solution was 5-5.5 and the solution contained 25%, 30% and 50% of methanol. Qualified effluents (purity ≥90%) were collected and pooled. About three column volumes of the effluent were collected, and then concentrated to dry.

Figure 7:
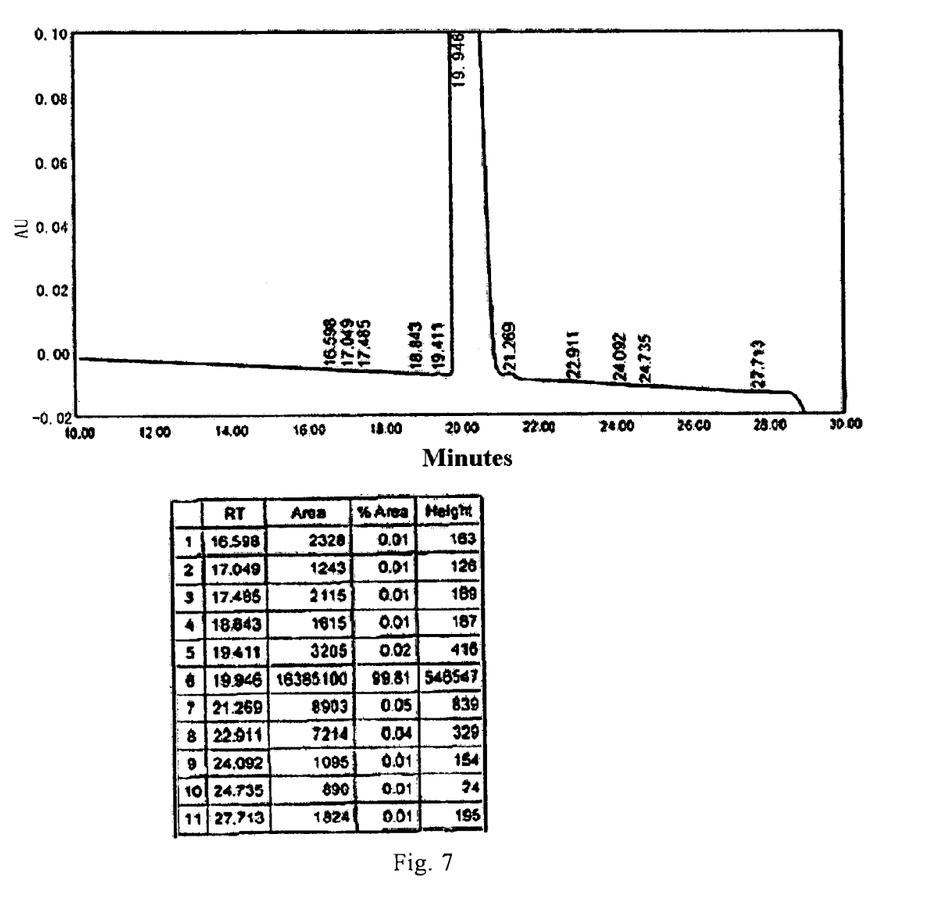
FIG. 7 shows the HPLC chromatogram of caspofungin acetate obtained according to Example 4 of the invention.

A white crystalline solid, i.e. caspofungin acetate (0.41 g, purity=99.81%), was obtained using the same crystallization procedure as described in Example 3 (FIG. 7).

Example 5

Purification of Compound 1

At a temperature below 20□, 30 mL reaction solution of compound 1 (obtained in Example 1) was diluted into 250 mL purified water. The pH was regulated to 5.0-5.5 with acetic acid. Adsorption was conducted using 100 mL pre-treated XAD-1600 resin at a flow rate of 1 L/h. The resin was washed with 300 mL 0.016% (V/V) acetic acid solution of pH 5-5.5 to remove organic phase. Then, the resin was eluted sequentially in three gradients with 0.016% (V/V) aqueous acetic acid solutions, wherein the pH of the solution was 5-5.5 and the solution contained 20%, 30% and 40% of acetone. Qualified effluents (purity ≥90%) were collected and pooled. About three column volumes of the effluent were collected, and then concentrated to dry.

A white crystalline solid, i.e. caspofungin acetate (0.51 g, purity=99.46%), was obtained using the same crystallization procedure as described in Example 3.

Example 6

Purification of Compound 1

At a temperature below 20□, 30 mL reaction solution of compound 1 (obtained in Example 1) was diluted into 250 mL purified water. The pH was regulated to 5.0-5.5 with acetic acid. Adsorption was conducted using 100 mL pre-treated HZ-803 resin at a flow rate of 1 L/h. The resin was washed with 300 mL 0.016% (V/V) acetic acid solution of pH 5-5.5 to remove organic phase. Then, the resin was eluted sequentially in three gradients with 0.016% (V/V) aqueous acetic acid solutions, wherein the pH of the solution was 5-5.5 and the solution contained 30%, 40% and 50% of acetone. Qualified effluents (purity ≥90%) were collected and pooled. About three column volumes of the effluent were collected, and then concentrated to dry.

A white crystalline solid, i.e. caspofungin acetate (0.58 g, purity=99.88%), was obtained using the same crystallization procedure as described in Example 3.

Example 7

Purification of Compound 1

At a temperature below 20□, 30 mL reaction solution of compound 1 (obtained in Example 1) was diluted into 250 mL purified water. The pH was regulated to 5.0-5.5 with acetic acid. Adsorption was conducted using 100 mL pre-treated LD-605 resin at a flow rate of 1 L/h. The resin was washed with 300 mL 0.016% (V/V) acetic acid solution of pH 5-5.5 to remove organic phase. Then, the resin was eluted sequentially in three gradients with 0.016% (V/V) aqueous acetic acid solutions, wherein the pH of the solution was 5-5.5 and the solution contained 20%, 40% and 50% of acetone. Qualified effluents (purity ≥90%) were collected and pooled. About three column volumes of the effluent were collected, and then concentrated to dry.

A white crystalline solid, i.e. caspofungin acetate (0.65 g, purity=99.90%), was obtained using the same crystallization procedure as described in Example 3.

Example 8

Purification of Compound 1

At a temperature below 20□, 160 mL reaction solution of compound 1 (obtained in Example 2) was diluted into 1440 mL purified water. Adsorption was conducted using 170 mL pre-treated HP20ss resin at a flow rate of 1 L/h. The resin was washed with 500 mL 0.016% (V/V) acetic acid solution of pH 5-5.5 to remove organic phase. Then, the macroporous adsorption resin was eluted sequentially in three gradients with 0.016% (V/V) aqueous acetic acid solutions, wherein the pH of the solution was 5-5.5 and the solution contained 10%, 20% and 25% of acetone. Qualified effluents (purity ≥90%) were collected and pooled. About four column volumes of the effluent were collected, and then concentrated to dry.

A white crystalline solid, i.e. caspofungin acetate (1.76 g, purity=99.71%), was obtained using the same crystallization procedure as described in Example 3.

Example 9

Purification of Compound 1

At a temperature below 20□, 160 mL reaction solution of compound 1 (obtained in Example 2) was diluted into 1440 mL purified water. Adsorption was conducted using 170 mL pre-treated HP20ss resin at a flow rate of 1 L/h. The resin was washed with 500 mL 0.016% (V/V) acetic acid solution of pH 5-5.5 to remove organic phase. Then, the resin was eluted sequentially in three gradients with 0.016% (V/V) aqueous acetic acid solutions, wherein the pH of the solution was 5-5.5 and the solution contained 25%, 30% and 50% of methanol. Qualified effluents (purity ≥90%) were collected and pooled. About three column volumes of the effluent were collected, and then concentrated to dry.

A white crystalline solid, i.e. caspofungin acetate (1.69 g, purity=99.61%), was obtained using the same crystallization procedure as described in Example 3.

Example 10

Purification of Compound 1

At a temperature below 20□, 160 mL reaction solution of compound 1 (obtained in Example 2) was diluted into 1440 mL purified water. Adsorption was conducted using 170 mL pre-treated XAD-1600 resin at a flow rate of 1 L/h. The resin was washed with 500 mL 0.016% (V/V) acetic acid solution of pH 5-5.5 to remove organic phase. Then, the resin was eluted sequentially in three gradients with 0.016% (V/V) aqueous acetic acid solutions, wherein the pH of the solution was 5-5.5 and the solution contained 20%, 30% and 40% of acetone. Qualified effluents (purity ≥90%) were collected and pooled. About three column volumes of the effluent were collected, and then concentrated to dry.

A white crystalline solid, i.e. caspofungin acetate (1.63 g, purity=99.01%), was obtained using the same crystallization procedure as described in Example 3.

Example 11

Purification of Compound 1

At a temperature below 20□, 160 mL reaction solution of compound 1 (obtained in Example 2) was diluted into 1440 mL purified water. Adsorption was conducted using 170 mL pre-treated HZ-803 resin at a flow rate of 1 L/h. The resin was washed with 500 mL 0.016% (V/V) acetic acid solution of pH 5-5.5 to remove organic phase. Then, the resin was eluted sequentially in three gradients with 0.016% (V/V) aqueous acetic acid solutions, wherein the pH of the solution was 5-5.5 and the solution contained 30%, 40% and 50% of acetone. Qualified effluents (purity ≥90%) were collected and pooled. About three column volumes of the effluent were collected, and then concentrated to dry.

A white crystalline solid, i.e. caspofungin acetate (1.70 g, purity=99.71%), was obtained using the same crystallization procedure as described in Example 3.

Example 12

Purification of Compound 1

At a temperature below 20□, 160 mL reaction solution of compound 1 (obtained in Example 2) was diluted into 1440 mL purified water. The pH was regulated to 5.0-5.5 with acetic acid. Adsorption was conducted using 170 mL pre-treated LD-605 resin at a flow rate of 1 L/h. The resin was washed with 500 mL 0.016% (V/V) acetic acid solution of pH 5-5.5 to remove organic phase. Then, the resin was eluted sequentially in three gradients with 0.016% (V/V) aqueous acetic acid solutions, wherein the pH of the solution was 5-5.5 and the solution contained 20%, 40% and 50% of acetone. Qualified effluents (purity ≥90%) were collected and pooled. About three column volumes of the effluent were collected, and then concentrated to dry.

A white crystalline solid, i.e. caspofungin acetate (1.68 g, purity=99.88%), was obtained using the same crystallization procedure as described in Example 3.

The above examples are merely the preferred examples for the present invention, and such examples cannot be used to limit the scope of the invention. The substantial technical contents according to the present invention are broadly defined in the claims. And any entities or methods accomplished by others should be considered as the equivalents and fall within the scope as defined by the claims, if said entities or methods are the same as those defined by the claims.

What is claimed is:

1. A purification process for the compound of Formula 1, wherein said process comprising:
   (1) loading a crude compound 1 onto a macroporous adsorption resin;
   (2) washing the macroporous adsorption resin with an aqueous solution, an organic solvent or a mixed solution of an organic solvent and water;
   (3) eluting with an aqueous solution, an organic solvent or a mixed solution of an organic solvent and water to give a purified compound of Formula 1;

1 wherein the macroporous adsorption resin is selected from a non-polar aromatic adsorption resin polymerized from styrene and divinylbenzene, or a moderately polar methacrylic adsorption resin comprising methacrylate unit in its structure;

the organic solvent is selected from methanol, ethanol, or $C_1$-$C_4$ ketone, the concentration gradient of the organic solvent is 10%-60% (v/v), and the pH of the aqueous solution, the organic solvent or the Mixed solution of an organic solvent and water is ≥7.

2. The purification process according to claim 1, wherein the macroporous adsorption resin is selected from one or more of the following resins: XAD-1, XAD-2, XAD-3, XAD-4, XAD-5, XAD-16, XAD-16HP; or from one or more of the following resins: HP-10, HP-20, HP-20ss, HP-21, HP-30, HP-40, HR-50, SP-825, SP-850, SP-70, SP-700, SP-207; or from one or more of the following resins: XAD-6, XAD-7, XAD-7HP, XAD-8; or HP-2MG.

3. The purification process according to claim 1, wherein step (3) is followed by:
   (4) crystallizing the purified compound of Formula 1 to give a compound of Formula 1 having a purity of greater than 99%.

4. The purification process according to claim 1, wherein the pH is 4.5-6.0.

5. The purification process according to claim 1, wherein the pH is 5.0-5.5.

6. The purification process according to claim wherein the concentration gradient of methanol or ethanol is 25%-50% (v/v).

7. The purification process according to claim 2, wherein the concentration gradient of methanol or ethanol is 25%, 30%, 50% (v/v).

8. The purification process according to claim 1, wherein the concentration gradient of $C_1$-$C_4$ ketone is 10%-50% (v/v).

9. The purification process according to claim 1, wherein the concentration gradient $C_1$-$C_4$ ketone is 10%, 20%, 25% (V/V); 20%, 30%, 40% (V/V); 30%, 40%, 50% (V/V); 20%, 40%, 50% (V/V); 10%, 20%, 25% (V/V); 20%, 30%, 40% (V/V); 30%, 40%, 50% (V/V); or 20%, 40%, 50% (V/V).

10. The purification process according to claim 1, wherein the $C_1$-$C_4$ ketone is acetone.

11. The purification process according to claim 1, wherein the aqueous solution the organic solvent and the mixed solution of an organic solvent and water contains 0.016% (V/V) acetic acid.

* * * * *